United States Patent [19]

Fortunato et al.

[11] Patent Number: 5,155,552
[45] Date of Patent: Oct. 13, 1992

[54] INTERFEROMETRIC DEVICE FOR DETECTING AND MEASURING THE CONCENTRATION OF AN ABSORBING GAS, PARTICULARLY IN THE INFRARED

[75] Inventors: Gerard Fortunato, Lyons; Dominique Laurent, Vienne, both of France

[73] Assignee: Societe Nationale Elf Aquitaine, Courbevoie, France

[21] Appl. No.: 455,001

[22] Filed: Dec. 22, 1989

[30] Foreign Application Priority Data

Dec. 23, 1988 [FR] France .............................. 88 17063

[51] Int. Cl.$^5$ .............................................. G01B 9/02
[52] U.S. Cl. ...................................... 356/346; 356/351
[58] Field of Search ........................ 356/51, 346, 351; 350/403, 404

[56] References Cited

U.S. PATENT DOCUMENTS

| | | | |
|---|---|---|---|
| 4,006,426 | 2/1977 | Lacour | 350/403 X |
| 4,320,973 | 3/1982 | Fortunato et al. | 356/346 |
| 4,732,480 | 3/1988 | Fortunato et al. | 356/351 X |

FOREIGN PATENT DOCUMENTS

| | | |
|---|---|---|
| 2340540 | 9/1977 | France . |
| 2555748 | 5/1985 | France . |
| 2566532 | 12/1985 | France . |

*Primary Examiner*—Samuel A. Turner

[57] ABSTRACT

An interferometric unit consisting of a birefringent plate combined with an isotropic plate.

This unit makes it possible to work with materials whose birefringence is slight and/or to reduce the necessary thickness of the birefringent plate. The unit is suited for integration into an interferometric device whose particular application is the detection of gases with quasi-periodic absorption structure absorbing in the infra-red.

18 Claims, 1 Drawing Sheet

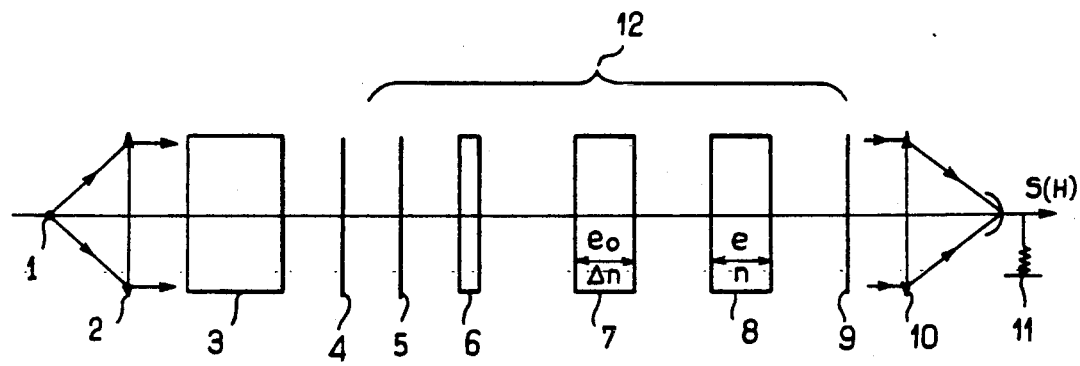
FIG._1
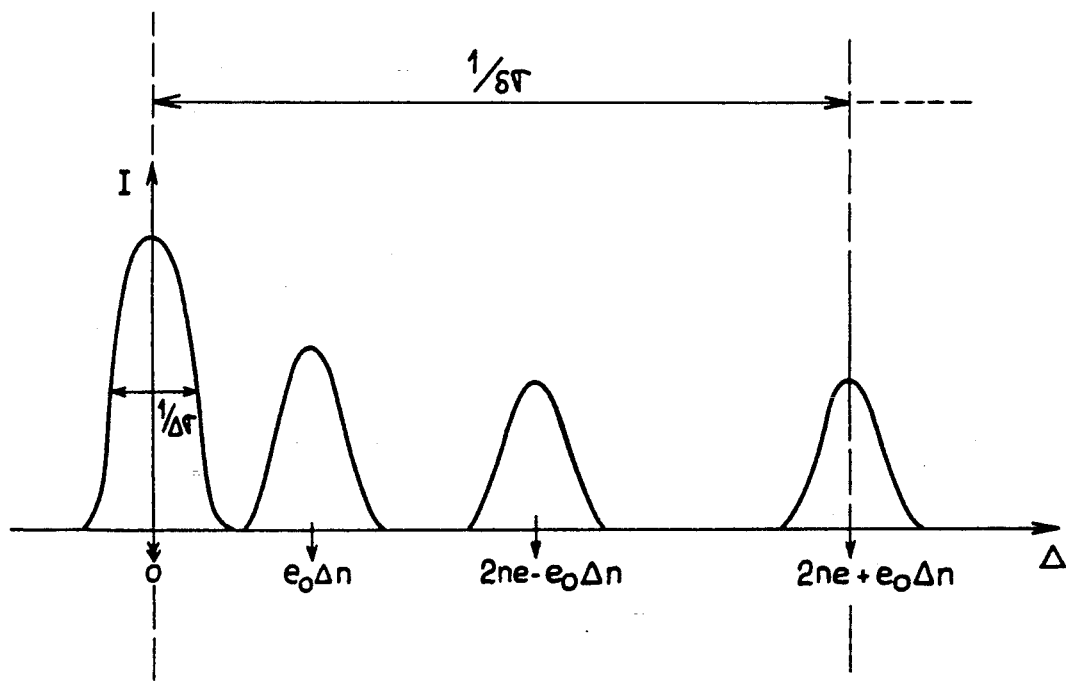
FIG._2

INTERFEROMETRIC DEVICE FOR DETECTING AND MEASURING THE CONCENTRATION OF AN ABSORBING GAS, PARTICULARLY IN THE INFRARED

BACKGROUND OF THE INVENTION

1. FIELD OF THE INVENTION

The present invention relates to a particular interferometric system and a device for detecting and measuring the concentration of a gas in a gaseous mixture, the absorption structure of said gas being quasi-periodic in a determined spectral band. The devices provided herein make it possible to use materials with slight birefringence and in particular are intended for analysis of gases in the infra-red.

1. DISCUSSION OF RELATED ART

Measurement of the concentration of a gas by the study of its absorption spectrum has been the object of several patents which are concerned with interferometric devices which utilize Fourier formalisms.

For a gas exhibiting locally, in a band of the scale of wave numbers, a quasi-periodic absorption spectrum of period p, the Fourier transform of the spectrum produced by an interferometric system placed in the path of a light ray, which has gone through a mixture containing the gas, exhibits a measurable maximum on the signal transmitted by the interferometric system for $\Delta_c = 1/p$, $\Delta_c$ being the path difference characterizing said system. This maximum reflects the similarity of the fringe system produced by the interferometric system to the fringe system of the absorption spectrum of the gas.

French patents published under numbers 2,340,540; 2,555,748; 2,566,748; 2,566,532 and 2,581,190 describe interferometric devices for detecting a gas in a mixture. These devices, in their simplest form comprise as an interferometer: a plate of birefringent material, of birefringence $\Delta_n$ and thickness e, cut for example, parallel to the axis of the material and providing a path difference $\Delta = e \cdot \Delta_n$. One of the simplest devices is described in the publication FR. A.2,340,540 and comprises successively along the same optical axis: a light source with continuous emission spectrum; a lens; a gas cell containing the mixture to be analyzed; a filter isolating the absorption band of the gas studied; a polarizer; a birefringent plate; an analyzer; a lens; a diaphragm located at the image focus of said lens; and a detector transforming the light energy into an electric signal, for example, a photoelectric multiplier, with which the interference phenomenon is studied. The thickness of the birefringent plate, which is adapted to the gas studied, is selected to obtain behind the lens an order of interferences corresponding to a maximum of illumination of the interference phenomena in the presence of the substance studied.

For an easy and precise reading of the output signal, the luminous flux is modulated by rotation of the polarizer or analyzer, to form alternately in the focal plane of the lens, a given fringe system or its complementary, when the polarizer and analyzer are parallel or perpendicular. The rotation of the analyzer or polarizer is made at frequency f, so that the interference term is modulated and the signal delivered by the detector exhibits a double frequency 2f. The amplitude of this output signal is proportional to the concentration of the gas studied, which is circulating in the cell placed in front of the interferometer.

The advantage of the above devices resides in their small size, their very great stability and the ease with which signals can be modulated, either by the rotation of the analyzer and polarizer, or else by rotation of a plate $\lambda/2$, or by use of a photoelastic modulator, or by vibration of a periodic grating.

The above devices' drawbacks reside in the fact that in the spectral regions studied, (i.e., in the region that comprises the absorption region of the gas or gases studied), it is not always easy to find materials for making the polarizers and analyzers and the birefringent plate, that allow the analyzer to be made at a low cost. This is thought particularly true in the case where the region studied is an infrared region between 2 microns and 8 microns.

In such an infrared region (i.e., 2–8 microns), the making of appropriate polarizers and analyzers can also pose problems. Absorption of films polarizing infrared does not allow for going beyond 2.5 microns. For example, calcite cannot be used beyond 2.5 microns because it becomes dichroic. Dichroic synthetic materials are known in business under the name of POLAROID ®, and are currently used in the visible and ultraviolet light regions, but cannot be used in the infrared light region A solution which allows one to go beyond 2.5 microns is given in French patent 2,581,190, the solution consists of resorting to polarizing prisms of the Wollaston type of quartz or magnesium fluoride. The main drawbacks of these polarizers are their high cost and the slight light range that they allow.

Still, more acute problems can arise in the making of a birefringent plate useful in the study of the infrared region. The following serves as an example of such problems. In the following example, it is assumed carbon monoxide (CO) is in the gas mixture analyzed.

To make a birefringent plate that can be used in the infrared, two materials in particular can be used: rutile with a birefringence $\Delta_n = 0.2$, and magnesium fluoride with a birefringence $\Delta_n = 10^{-2}$. At 4.6 microns CO exhibits an absorption band with a fine absorption structure with periodicity 67 $\sigma = ^2\text{cm}^{-1}$. The thickness of the plate necessary in this case is $e_o$, so that $e_o \Delta_n = 1/\delta\sigma$ which gives a thickness equal either to 500 mm in the case of the magnesium fluoride plate, which is impossible to achieve, or to 25 mm in the case of the rutile plate, which is impossible to envisage in ,industry because of the prohibitive cost associated with the production of a plate of such a thickness.

Thus, it is the fact that the required thicknesses and costs are too great and/or the fact that the birefringence of the materials usable (for example in the infrared) is too slight, which has led to the impossibility of making an interferometric analysis device using a birefringent plate as briefly described above and described in greater detail in the French patent 2,340,540.

SUMMARY OF THE INVENTION

The present invention, while maintaining the advantages of the devices of the prior art, makes it possible to avoid drawbacks occurring in the prior art and has an object to compensate for the slight birefringence of certain materials usable for making birefringent plates, in particular those necessary for making the family of devices referenced above, and to reduce the thickness of said plates.

The above object is achieved thanks to an interferometric system combining: a birefringent plate, as described above, which makes it possible to retain ease of modulation; and an isotropic plate consisting of a plate with parallel faces with sufficiently great reflection coefficients, for example $\geq 0.3$. Such an isotropic plate makes it possible to create, from an incident ray, two transmitted rays, a first one directly, and a second one after-internal reflection on each of the two faces of the plate. The path difference between the two transmitted rays being $\Delta = 2n \cdot e$ where n is the index of the material used for the isotropic plate and e is its thickness.

The association of the birefringent plate and the isotropic plate results in a splitting of the number of rays obtained with a single birefringent plate, so that, at the output, path differences higher than that obtained with the single birefringent plate are obtained, thus reducing the necessary thickness of the birefringent plate.

For detecting and measuring the concentration of at least one gas in a gaseous mixture, the interferometric system of the present invention is integrated into an optical device comprising, on the same optical axis:

a broad spectrum light source whose light beam is focused at infinity by a first focusing lens, passed through a gas cell containing a circulating gas mixture, which comprises the gas to be analyzed; an interferential filter for isolating the specific spectral band of the gas studied; a polarizer; a modulator; a birefringent plate; an isotropic plate; an analyzer; a second focusing lens and a detector located in the focal plane of said second lens The order in which the modulator, birefringent plate and isotropic plate are placed between the polarizer and analyzer is not considered important.

Other characteristics and advantages of this invention will come out more clearly from reading the following descriptions.

BRIEF DESCRIPTION OF THE DRAWINGS

FIG. 1 illustrates diagrammatically a unit of the device according to the present invention.

FIG. 2 diagrams, as a function of the path difference, the zones for which a usable signal of intensity I is obtained.

DETAILED DESCRIPTION OF THE INVENTION

In one embodiment, intended more particularly for the infrared, the device for detecting and measuring the concentration of at least one gas contained in a gaseous mixture, as represented in FIG. 1, comprises a light source 1, which can be a globar, a lens 2, gas cell 3, an interferential filter 4 isolating the infrared, band, a polarizer 5, a modulator 6, a birefringent plate 7, an isotropic plate 8, an analyzer 9, a focusing lens 10 and a detector 11. The polarizer and analyzer are unidirectional and are periodic gratings, the period being adapted to the frequency region studied, which are parallel or perpendicular to one another, and are both placed at 45 degrees from the axes of birefringent plate 7 and modulator 6. Isotropic plate 8 is of thickness e and index n, thereby creating a path difference $\Delta = 2n\,e$. The isotropic plate has parallel faces that can be coated with a nonabsorbing dielectric deposit with transmission coefficient $T_1$ and reflection coefficient $R_1$ for the first face turned toward the source, and with transmission and reflection coefficient $T_2$ and $R_2$, respectively, for the second face turned toward the detector. The isotropic plate can be made of fluorine and the reflecting treatment of the faces can be achieved by deposit of silica. Birefringent plate 7, of thickness $e_o$ and birefringence, $\Delta_n$ can be made of magnesium fluoride, which is much less costly than rutile.

Modulator 6 has the role of modifying periodically the optical path difference caused by the birefringent and isotropic plates 7 and 8, to modulate only the interference term that contains the quantitative data on the presence of the gas studied. The modulator can be a photoelastic modulator comprising a silica or fluorine plate excited by a piezoelectric ceramic to give said plate a variable birefringence by compression. The lenses 2 and 10 and windows of the gas cell 3 can be made of fluorine. Detector 11 delivers a signal that is processed by synchronous detection of the frequency of the modulator. The modulator provides a continuous signal whose level is proportional to the concentration of the gas studied.

Such a unit provides an intensity I so that $$I = \frac{T_1 T_2}{4}\left[1 + R_1 R_2 + (1 + R_1 R_2)\cos\frac{2\pi}{\lambda}[e_o\,\Delta n + \delta(t)] + \right.$$

$$\sqrt{R_1 R_2}\,\cos\frac{\ln}{\lambda}\,2\pi e +$$

$$\frac{1}{2}\sqrt{R_1 R_2}\,\cos\frac{2\pi}{\lambda}[2ne + e_o\,\Delta_n{'} + \delta(t)] +$$

$$\left. \frac{1}{2}\sqrt{R_1 R_2}\,\cos\frac{2\pi}{\lambda}[2ne - e_o\,\Delta n - \delta(t)]\right]$$

where (t) is the path difference that varies as a function of time and is introduced by the photoelastic modulator. As diagrammed in FIG. 1, such a unit provides, from one incident ray, four transmitted rays, three of which exhibit, relative to the first, path differences whose values, in increasing order, deduced from expression of intensity I given above, are :

$e_o \cdot \Delta n,\; 2n\cdot e - e_o\Delta_n,\; 2n\cdot e + e_o\Delta n$

It is known that if a source has a spectral width $\Delta\sigma$, or a spectral half width where $\Delta = 1/\Delta\sigma$, there are obtained, with an isotropic interferometer (which is a two-wave interferometer), central fringes, in the vicinity of $\Delta = 0$, which do not contain any interesting data.

For infrared application, the path difference $e_o\,\Delta_n$ is small, as noted above, and it is necessary to avoid a grouping around $\Delta = 0$ of the regions where useful data exists. As such, it is thought necessary to group data as diagrammed in FIG. 2, around values of $\Delta$ equal to $e_o\Delta_n$, $2n\,e - e_o\Delta_n$ and $2n\,e + e_o\Delta_n$. In this regard, it is also thought necessary to choose $e_o$ so that $e_o\,\Delta_n > 1/\Delta\sigma$. On the other hand, $\delta\sigma$ being the periodicity of the spectrum, useful data will also be repeated at frequency $\delta\sigma$. To avoid an overlapping of these different data areas by one another, which would make analysis of the results difficult, it is also thought necessary to select thickness e of the isotropic plate so that $2n\,e + e_o\,\Delta_n \leq 1/\delta\sigma$.

Let us take as an example carbon monoxide (CO), whose absorption structure exhibits a periodicity $\delta\sigma = 2\,\mathrm{cm}^{-1}$ on a band $\Delta\sigma = 200\ \mathrm{cm}^{-1}$. For a fluorine isotropic plate with index n $= 1.4$ and thickness $e = 1.7$ mm, it suffices to provide a magnesium fluoride birefringent plate with a thickness $e_o = 8$ mm (instead of $e_o = 500$ mm which would be needed without the isotropic plate!).

A particular field of application of the devices according to the present invention, is in the analysis of gases whose quasi-periodic absorption region is located in the infrared. The devices of the present invention allows one to perform such analysis while being stable, of low cost and being compact.

Of course, the invention is not limited to the embodiments described and represented herein, and it is capable of numerous variations accessible to those skilled in the art without going outside the spirit of the present invention. The present invention is only to be limited by the scope of the appended claims.

What is claimed is:

1. An interferometric system which creates from one incident light ray, two or more transmitted rays, all of which exhibit among them path differences, the system consisting of an interferometer with a combination of a birefringent plate and an isotropic plate on a single optical axis.

2. An interferometric system according to claim 1, wherein the birefringent plate is made of magnesium fluoride and the isotropic plate of fluorine.

3. An interferometric device for detecting and measuring the concentration of at least one gas in a gas mixture, the gases exhibiting a quasi-periodic absorption structure, said device comprising the following components on a single optical axis;

a light source whose beam successively goes through a first lens; a gas cell; a frequency filter; a polarizer; an interferometry and modulation unti; an analyzer and a second lens before reaching a detector; wherein said interferometric and modulation unit consists of the interferometric system according to claim 1.

4. The interferometric device of claim 3, wherein said interferometry and modulation unit further consists of a modulator of said single optical axis, said modulator, said birefringent plate and said isotropic plate being arranged along said single optical axis in a sequential order selected from a group consisting of (a) said modulator, said birefringent plate and said isotropic plate;
(b) said birefrigent plate, said isotropic plate and said modulator;
(c) said isotropic plate, said modulator and said birefringent plate;
(d) said modulator, said isotropic plate and said birefringent plate;
(e) said birefringent plate, said modulator and said isotropic plate; and
(f) said isotropic plate, said birefringent plate and said modulator.

5. The interferometric system of claim 1, wherein the faces of said isotropic plate have reflection coefficients $\geq 0.3$.

6. The interferometric system of claim 2, wherein the faces of said isotropic plate have reflection coefficients $\geq 0.3$.

7. The interferometric device of claim 3, wherein the faces of said isotropic plate have reflection coefficients $\geq 0.3$.

8. The interferometric device of claim 3, wherein the faces of said isotropic plate have reflection coefficients $\geq 0.3$.

9. A method for detecting and measuring the concentration of at least one gas in a gas mixture, the gases exhibiting a quasi-periodic absorption structure, said method comprising:

passing a broad spectrum light beam through; a first lens; a gas cell; a frequency filter; a polarizer; an interferometry and modulation unit which comprises a combination of a birefringent plate and an isotropic plate on a single optical axis; an analyzer; and a second lens.

10. The method of claim 9, wherein said unit further comprises a modulator on said single optical axis, said modulator, said birefringent plate and said isotropic plate being arranged along said single optical axis in a sequential order selected from a group consisting of (a) said modulator, said birefringent plate and said isotropic plate;
(b) said birefrigent plate, said isotropic plate and said modulator;
(c) said isotropic plate, said modulator and said birefringent plate;
(d) said modulator, said isotropic plate and said birefrigent plate;
(e) said birefringent plate, said modulator and said isotropic plate; and
(f) said isotropic plate, said birefringent plate and said modulator.

11. The method of claim 9, wherein said birefringent plate is made of magnesium fluoride and said isotropic plate is made of fluorine.

12. The method of claim 10, wherein said birefringent plate is made of magnesium fluoride and said isotropic plate is made of fluoride.

13. The method of claim 9, wherein the faces of said isotropic plate have reflection coefficients $\geq 0.3$.

14. The method of claim 10, wherein the faces of said isotropic plate have reflection coefficients $\geq 0.3$.

15. The method of claim 11, wherein the faces of said isotropic plate have reflection coefficients $\geq 0.3$.

16. The method of claim 12, wherein the faces of said isotropic plate have reflection coefficients $\geq 0.3$.

17. The method of claim 9, wherein said gases exhibit a quasi-periodic absorption structure absorbing in the infra-red.

18. The method of claim 10, wherein said gases exhibit a quasi-periodic absorption structure absorbing in the infra-red.

* * * * *

UNITED STATES PATENT AND TRADEMARK OFFICE
CERTIFICATE OF CORRECTION

PATENT NO. : 6,155,552
DATED : December 5, 2000
INVENTOR(S) : Katsuaki Hirai, et al.

It is certified that error appears in the above-identified patent and that said Letters Patent is hereby corrected as shown below:

Title page,
Item[30], "Oct. 2, 1995" should read -- Sept. 30, 1994 --.
Item[57], Abstract line 6, "doe snot" should read -- does not --.

Column 5,
Line 43, "prevented" should read -- be prevented --.

Column 15,
Line 35, "take" should read -- takes --.

Column 16,
Line 10, "reversal" should read -- reversed --; and
Line 18, "repetitive" should read -- repeat --.

Column 19,
Line 45, "through" should read -- though --.

Column 22,
Line 27, "said" should read -- said sheet set --;
Line 43, "is" should read -- are --;
Line 56, "apparatus," should read -- apparatus --;
Line 56, "claim 1 that" should read -- claim 1, wherein --; and
Line 57, "stop" should read -- stops --.

UNITED STATES PATENT AND TRADEMARK OFFICE
CERTIFICATE OF CORRECTION

PATENT NO. : 6,155,552
DATED : December 5, 2000
INVENTOR(S) : Katsuaki Hirai, et al.

It is certified that error appears in the above-identified patent and that said Letters Patent is hereby corrected as shown below:

<u>Column 23,</u>
Line 25, "is" should read -- are --;
Line 46, "being" should read -- is -- and "sheet" should read -- said sheet --;
Line 47, "driving" should read -- shift --;
Line 62, "is" should read -- are --;
Line 63, "180x" should read -- 180° --; and
Line 67, "stop" should read -- stops --.

Signed and Sealed this

Second Day of October, 2001

Attest:

NICHOLAS P. GODICI
Attesting Officer     Acting Director of the United States Patent and Trademark Office